United States Patent [19]

Schultz et al.

[11] Patent Number: 4,777,529

[45] Date of Patent: Oct. 11, 1988

[54] AUDITORY SUBLIMINAL PROGRAMMING SYSTEM

[75] Inventors: Richard M. Schultz, Marengo; Raymond Dolejs, Arlington Heights, both of Ill.

[73] Assignee: R. M. Schultz & Associates, Inc., McHenry, Ill.

[21] Appl. No.: 76,113

[22] Filed: Jul. 21, 1987

[51] Int. Cl.[4] .............................................. H04N 5/92
[52] U.S. Cl. ..................... 358/143; 358/341; 380/23; 381/73.1; 381/105; 381/124; 434/307; 434/319
[58] Field of Search ........................ 358/93, 143, 341; 380/23; 381/73.1, 105, 124; 434/307, 319

[56] References Cited

U.S. PATENT DOCUMENTS

| | | |
|---|---|---|
| 2,338,551 | 7/1942 | Stanko . |
| 2,409,058 | 12/1944 | Mitchell . |
| 2,501,327 | 3/1950 | Good . |
| 2,941,044 | 6/1980 | Volkmann . |
| 3,060,795 | 10/1962 | Corrigan et al. . |
| 3,173,136 | 3/1965 | Atkinson . |
| 3,278,676 | 10/1966 | Becker . |
| 3,410,958 | 11/1968 | Cohen . |
| 3,579,233 | 5/1971 | Raschke . |
| 3,934,084 | 1/1976 | Munson et al. . |
| 3,934,085 | 1/1976 | Munson et al. . |
| 4,052,720 | 10/1977 | McGregor et al. . |
| 4,061,874 | 12/1977 | Frick et al. . |
| 4,124,943 | 11/1978 | Mitchell ............................... 434/307 |
| 4,230,990 | 10/1980 | Lert ........................................ 358/84 |
| 4,270,284 | 6/1981 | Skellings .............................. 434/169 |
| 4,315,502 | 3/1982 | Gorges . |
| 4,373,918 | 2/1983 | Berman ................................ 434/307 |
| 4,395,600 | 7/1983 | Lundy .................................. 381/73.1 |
| 4,396,946 | 9/1983 | Bond . |
| 4,699,153 | 10/1987 | Shevrin ................................ 128/731 |
| 4,717,343 | 1/1988 | Densky ................................ 434/262 |

*Primary Examiner*—Howard W. Britton
*Attorney, Agent, or Firm*—Willian Brinks Olds Hofer Gilson & Lione Ltd.

[57] ABSTRACT

An auditory subliminal programming system includes a subliminal message encoder that generates fixed frequency security tones and combines them with a subliminal message signal to produce an encoded subliminal message signal which is recorded on audio tape or the like. A corresponding subliminal decoder/mixer is connected as part of a user's conventional stereo system and receives as inputs an audio program selected by the user and the encoded subliminal message. The decoder/mixer filters the security tones, if present, from the subliminal message and combines the message signals with selected low frequency signals associated with enhanced relaxation and concentration to produce a composite auditory subliminal signal. The decoder/mixer combines the composite subliminal signal with the selected audio program signals to form composite signals only if it detects the presence of the security tones in the subliminal message signal. The decoder/mixer outputs the composite signal to the audio inputs of a conventional audio amplifier where it is amplified and broadcast by conventional audio speakers.

21 Claims, 2 Drawing Sheets

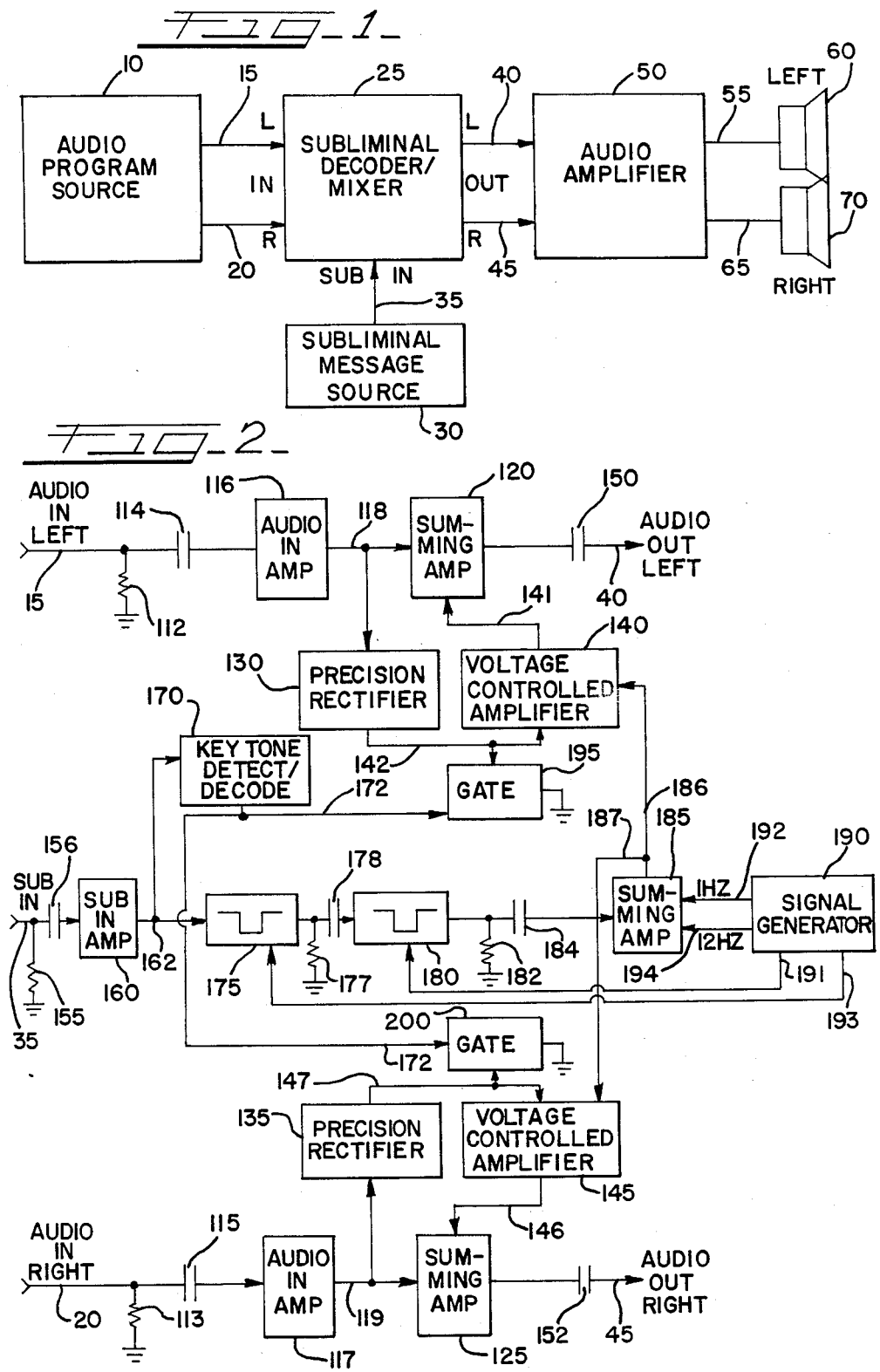

AUDITORY SUBLIMINAL PROGRAMMING SYSTEM

BACKGROUND OF THE INVENTION

1. Field of the Invention

This invention relates generally to systems for generating auditory subliminal messages. More particularly, the invention relates to an auditory subliminal programming system that includes security coding and decoding and improved automatic gain control of the subliminal message signal. The programming system of the invention is particularly well adapted for use in self-improvement programs.

2. Statement of Related Art

It has long been thought that subliminal programming has the capability to influence the behavioral patterns of listeners. Corrigan et al. U.S. Pat. No. 3,060,795 and Becker U.S. Pat. No. 3,278,676 are examples of early work in this area.

One application of auditory subliminal programming to influence the behavior of listeners has been in the area of anti-theft systems. Lundy et al. U.S. Pat. No. 4,395,600 discloses an anti-shoplifting system in which subliminal anti-shoplifting messages are mixed with audio program signals such as background music, and with a masking signal. The combined signal is then broadcast via loudspeakers to various areas of a store. In order to ensure that the subliminal message is broadcast at a sufficient level to be physically (although not conciupously) audible, Lundy et al. varies the amplitude of the subliminal signal as a function of the level of ambient noise in the store. However, in order to ensure that the subliminal message does not become supraliminal, i.e., consciously audible, during a sharp drop in the ambient noise level, Lundy et al. also uses a masking signal that quickly responds to changes in the ambient noise level to mask the subliminal message and prevent such an occurrence. The amplitude of the audio program signal i.e., the background music, is separately controlled independently of the ambient noise level.

It is also though that auditory and/or visual stimulation at certain frequencies enhances the relaxation, awareness, and control of the person being stimulated. See, for example, Gorges U.S. Pat. No. 4,315,502. The use of such stimulation in conjunction with auditory subliminal programming is desirable to further enhance the programming. However, insofar as the applicant is aware, no system combining auditory subliminal programming with such stimulation has heretofore been developed.

In particular, an area in which auditory subliminal programming alone or in combination with such other stimulation can be quite effective and beneficial is the area of self-improvement programming. For example, auditory subliminal programming can be used to help the listener stop smoking, lose weight, improve problem solving techniques, and the like.

In the past, tapes or other audio storage media having pre-recorded subliminal self-improvement messages mixed with pre-recorded audio programs such as musical programs have been available. The listener purchased the tapes and played them through his own home stereo, for example, to obtain the desired subliminal programming. However, this proved unsatisfactory to users primarily because they had no control over the musical selections provided and because the musical selections could not be changed.

Known prior art systems, such as the Lundy et al. system also have various drawbacks and lack certain features that have made them unsatisfactory for use in the personal self-improvement programming area. For instance, although it is desirable for the level of the subliminal message to track the higher level of the audio program, thereby optimizing the effect of the programming, it is unsatisfactory to do so by sensing the ambient noise level in a location such as the user's living or family room. In addition, the known systems do not include the very desirable feature of built-in security in order to inhibit unauthorized and possibly damaging use of the subliminal programming.

In view of the foregoing drawbacks and deficiencies of the prior art, it is an object of the present invention to provide an improved auditory subliminal programming system which is particularly well adapted for use in personal self-improvement programming.

It is another object of the invention to provide such a system which combines auditory subliminal programming with auditory stimulation at frequencies which enhance the relaxation, awareness and control of the listener for enhanced learning and retention.

It is a further object of the invention to provide such a system which includes built-in security measures which automatically prevent the use of unauthorized subliminal program material.

It is still another object of the invention to provide such a system wherein the quality of the composite signal containing the audio program and subliminal programming signals is enhanced by automatically controlling the relative level of the subliminal programming signal as a direct function of the amplitude of the audio program signal.

SUMMARY OF THE INVENTION

The foregoing objects and attendant advantages are obtained by providing a subliminal decoder/mixer that receives audio program signals and subliminal message signals, automatically varies the amplitude of the subliminal message signals as a function of the amplitude of the audio program signals, and combines the signals into a composite signal in which only the audio program component is consciously audible.

With respect to another aspect of the invention, the decoder/mixer detects whether at least one predetermined security code is present in the subliminal message signals and prevents combination of the audio program signals and subliminal message signals unless such code is detected.

With respect to still another aspect of the invention, the decoder/mixer combines the subliminal message signal with at least one signal having selected frequency to produce composite subliminal signals.

A subliminal message encoder system is also provided that generates at least one predetermined security code, combines the code with subliminal message signals generated by an audio source and records the encoded subliminal message signals.

With respect to yet another aspect, the decoder/mixer is combined with an audio program source, a subliminal message source, an audio amplifier and audio speakers to provide an auditory subliminal programming system.

In another variation, the decoder/mixer is combined with an audio-video program source, a composite video signal modulator, and a television video display to provide an audio-video subliminal programming system.

BRIEF DESCRIPTION OF THE DRAWING

The novel features that are believed to be characteristic of the invention are set forth in the appended claims. The invention itself, along with the foregoing objects and attendant advantages thereof, will be best understood by reference to the following detailed description of the presently preferred embodiments thereof, taken in conjunction with the drawing, in which:

FIG. 1 is a block diagram illustrating a presently preferred subliminal decoder/mixer, which embodies various novel features of the invention, together with related audio components;

FIG. 2 is an electrical schematic diagram illustrating the details of the subliminal decoder/mixer of FIG. 1;

DETAILED DESCRIPTION OF THE PRESENTLY PREFERRED EMBODIMENTS

Figure 3:
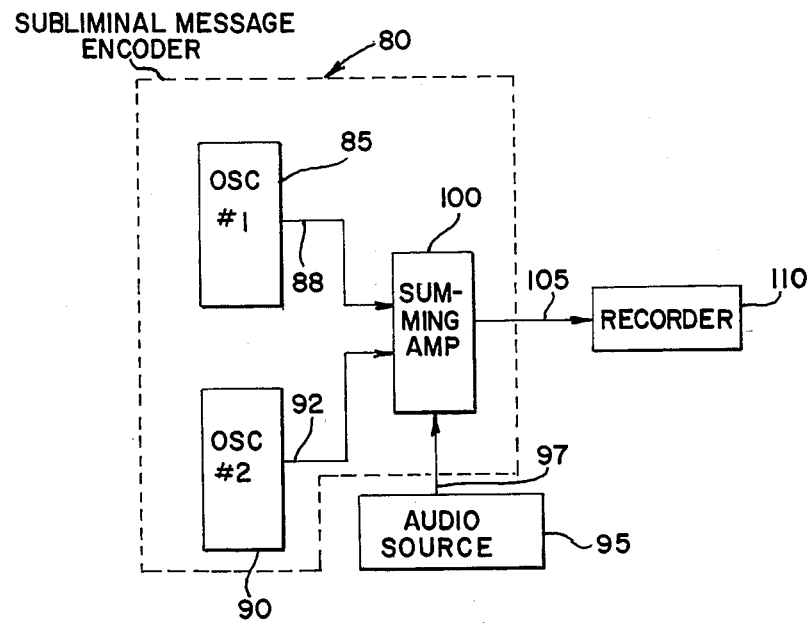
FIG. 3 is a block diagram illustrating a preferred subliminal message encoder which embodies various novel features of the invention, together with related audio components.

Referring to FIG. 1 of the drawing, an audio program source 10 such as a conventional tape deck, compact disc, or phonograph generates stereo music or other audio program signals selected by the user on left and right audio outputs. These signals are conducted to left and right audio inputs of a subliminal decoder/mixer 25 on lines 15 and 20 respectively.

A subliminal message source 30, which is typically also a tape deck, compact disc player, or other audio source generates a pre-determined subliminal message signal which is transmitted to a subliminal signal input of the subliminal decoder/mixer 25 on a line 35. The subliminal decoder/mixer 25 decodes the subliminal message signal and detects whether it contains two selected pre-recorded security tones. The subliminal decoder/mixer 25 filters the tones, if present, out of the subliminal message signal and mixes the subliminal message signal with the left and right audio program signals only if both tones are present. The subliminal decoder/mixer 25 also controls the level of the subliminal message signal as a function of the level of the audio program signal, mixes in two subliminal low frequency signals, and outputs the resulting composite signals on left and right audio output channels respectively.

The composite signals on the left and right audio output channels are transmitted to the left and right audio input channels of a conventional stereo amplifier 50 on lines 40 and 45 respectively. The amplifier 50 amplifies the composite signals and outputs them on lines 55 and 65 respectively to conventional left 60 and right 70 audio speakers. The listener consciously hears only the audio program he has selected, but subconsciously also receives the subliminal programming message and the subsonic frequency stimulation. If the user attempts to use an unauthorized subliminal message which does not contain both security tones, the decoder/mixer 25 detects the absence of the tones and does not mix the unauthorized message with the audio program.

FIG. 2 is an electrical schematic diagram which illustrates the details of the subliminal decoder/mixer 25 of FIG. 1. The decoder/mixer 25 has three inputs: a subliminal program signal input on line 35, a left audio signal input on line 15, and a right audio signal input on line 20. Power is supplied to the components by any conventional power supply (not shown) that is capable of full wave rectifying and filtering a 60 Hz AC power signal and providing $+/-12$ V and $+/-5$ V DC operating voltages therefrom.

An RC network comprised of resistor 155 connected between line 35 and ground and a series capacitor 156 couples line 35 to the input of a conventional audio input amplifier 160, which is suitably a conventional negative feedback operational amplifier. The output of the amplifier 160 is connected by line 162 to the signal input of a first notch filter 175. The output of the first notch filter 175 is coupled to the input of a second notch filter 180 through an RC network comprised of a resistor 177 connected between the output of the notch filter 175 and ground, and a series capacitor 178. The output of the second notch filter 180 is coupled to one input of a conventional summing amplifier 185 through an RC network comprised of a resistor 182 connected between the output of the second notch filter 180 and ground, and a series capacitor 184. The notch filters 175 and 180 may be either digital or analog filters, one tuned to each security tone frequency. A suitable digital notch filter, for example, is the MF10 notch filter manufactured by National Semiconductor Corp.

The output of the amplifier 160 is also connected by line 162 to the input of a security tone detect/decode unit 170. The output of the security tone detect/decode unit 170 is connected by a line 172 to the respective control terminals of a pair of transmission gates 195 and 200 respectively which are connected between lines 142 and 147 respectively and ground. The security tone detect/decode unit 170 is preferably comprised of two parallel phase locked loops (PLL's) (not shown) each tuned to one of the security tones. Line 162 is connected to the signal inputs of both PLL's and the tone detect signal outputs of the PLL's are gated together so that the output signal of the security tone detect/decode unit 170 on line 172 is low only if both security tones are present. The PLL's are suitably NE567 PLL's manufactured by a number of companies including Signetics, National Semiconductor, and Motorola.

A signal generator 190 preferably generates 1 Hz and 12 Hz TTL output pulses on lines 192 and 194 respectively. Lines 192 and 194 are connected to inputs of the summing amplifier 185. The signal generator 190 also preferably generates tuning frequency pulses which correspond to the frequencies of the selected security tones and outputs them to the notch filters 175 and 180 on lines 193 and 191 respectively. The signal generator 190 is preferably comprised of a conventional oscillator (not shown) having its output connected to one or more conventional counters (not shown) which count down the oscillator signals to provide the output signals on lines 191–194 having the desired frequencies. This technique is well known to those skilled in the art.

The output of the summing amplifier 185 is connected by lines 186 and 187 tpo the signal inputs of voltage controlled amplifiers 140 and 145 respectively. The signal outputs of the voltage controlled amplifiers 140 and 145 are connected by lines 141 and 146 respectively to inputs of conventional summing amplifiers 120 and 125 respectively.

An RC network comprised of resistor 112 connected between left audio input line 15 and ground and series capacitor 114 couples line 15 to the input of a conventional audio input amplifier 116. Likewise, an RC network comprised of a resistor 113 connected between the right audio input line 20 and ground, and a series capacitor 115 couples line 20 to the input of a conventional audio input amplifier 117. Audio input amplifiers 116 and 117 may also be conventional negative feedback operational amplifiers. The outputs of the audio input amplifiers 116 and 117 are connected by lines 118 and 119 respectively to the signal inputs of conventional precision rectifiers 130 and 135 respectively, and to signal inputs of the summing amplifiers 120 and 125 respectively. The outputs of the precision rectifiers 130 and 135 are connected by lines 142 and 147 respectively to the control terminals of the voltage controlled amplifiers 140 and 145 respectively and to signal inputs of the transmission gates 195 and 200 respectively. The outputs of the summing amplifiers 120 and 125 are coupled through series capacitors 150 and 152 respectively to left and right audio output lines 40 and 45 respectively.

Many suitable precision rectifiers are known to those skilled in the art. One such rectifier which utilizes a two-stage operational amplifier arrangement and which is suitable for use is illustrated and described in Roberge, *Operational Amplifiers Theory and Practice*, 458–460, John Wiley & Sons Inc. (1975). It is preferred, however, that in the illustrated rectifier circuit, the transistor in the negative feedback path of the first stage amplifier be replaced by a diode and that the fixed resistor in the negative feedback path of the second stage amplifier be replaced by a variable resistor to provide gain control. Suitable voltage controlled amplifiers are LM1035 amplifiers manufactured by National Semiconductor Corp.

FIG. 3 illustrates a presently preferred subliminal message encoding arrangement for use with the decoder/mixer 25 of FIGS. 1 and 2. A subliminal message encoder 80 includes a first oscillator 85, a second oscillator 90, and a summing amplifier 100. The first and second oscillators 85 and 90 respectively generate at their outputs first and second security tones having predetermined fixed frequencies. The outputs of the first and second oscillators 85 and 90 are connected by lines 88 and 92 respectively to signal inputs of a conventional summing amplifier 100. The output of the summing amplifier 100 is connected by a line 105 preferably to a signal input of a tape recorder, compact disc recorder or other audio recording device.

An audio source 95, which may be a person speaking through a microphone, or a tape recorder or speech synthesizer or the like, generates at its output subliminal message signals that will eventually be broadcast to the listener. The output of the audio source 95 is connected by a line 97 to a signal input of the summing amplifier 100.

The use and operation of the preferred auditory subliminal programming system will now be described. Initially the manufacturer of the subliminal message encoder and the subliminal decoder/mixer 25 determines the number and frequency of security tones that will be used. In the preferred embodiment, two tones are used. During manufacturing, the manufacturer tunes the PLL's of the detect/decode unit 170 and the notch filters 175 and 180 to the selected frequencies, and sets the oscillators 85 and 90 to the selected frequencies. The manufacturer uses the subliminal message encoder to produce tapes, compact disks or the like with the subliminal message and the security tones encoded thereon. Since only the manufacturer knows the tones selected, it retains control over the content of the subliminal programming which will be allowed to pass through the decoder/mixer 25.

Persons desiring to receive particular subliminal programming must obtain a subliminal decoder/mixer 25 and the tapes or other audio media containing the desired programming from the manufacturer. The user can verify the contents of the tapes or other media by playing them on a tape deck, compact disc player or other suitable audio reproduction equipment and listening to their contents. To use the subliminal decoder/mixer 25, the user plugs the left and right audio output jacks of his tape deck, compact disc player or other audio program source into the left and right audio inputs of the decoder/mixer 25. The user connects the left and right audio outputs of the decoder/mixer 25 to the left and right audio inputs of his stereo or audio amplifier. The user also connects an output of another tape deck or other suitable audio reproduction equipment which will be the subliminal message source to the subliminal signal input of the decoder/mixer 25. The user then plays whatever musical or other audio programs he selects on the tape deck connected to the audio inputs of the decoder/mixer 25, and the subliminal program material on the tape deck or other audio source connected to the subliminal signal input of the decoder/mixer 25. The user may control the volume of the audio program using the volume control provided on the tape deck and the decoder/mixer 25 automatically adjusts the level of the subliminal message signal as a function of the level of the audio program signals.

Referring to the details of the decoder/mixer 25 illustrated in FIG. 2, the RC networks comprised of resistors 112,113 and capacitors 114,115 AC couple the left and right audio program signals to the inputs of the audio input amplifiers 116 and 117 respectively. The audio input amplifiers 116 and 117 amplify the left and right audio signals and output the amplified signals to the summing amplifiers 120 and 125 on lines 118 and 119 respectively. Assuming that the subliminal message source 30 is not activated so that there is no subliminal message signal on line 35, the left and right audio signals pass through summing amplifiers 120 and 125 and are output on lines 40 and 45 unchanged. The gains of the audio input amplifiers 116 and 117 and the summing amplifiers 120 and 125 are preferably adjusted to provide unity gain to the left and right audio signals.

When a subliminal message signal is present on line 35, it is AC coupled to the input of the audio input amplifier 160 through the RC network comprised of resistor 155 and capacitor 156. The signal is amplified and output on line 162 to the series notch filters 175 and 180.

The series notch filters 175 and 180 remove the security tone frequencies from the subliminal message signal before it is input to the summing amplifier 185. The summing amplifier 185 sums the filtered subliminal message signal with the 1 Hz and 12 Hz stimulation signals generated by the signal generator 190. The 12 Hz signal component assists the listener in generating alpha brain waves which increase awareness. The 1 Hz component reinforces relaxation and concentration. If desired, either or both signals can also be transmitted through light emitting diodes (LED's) to provide visual as well as auditory stimulation.

In order to maintain the subliminal message at an optimum level with respect to the level of the audio program, the voltage controlled amplifiers 140 and 145 control the amplitude of the subliminal signal output by the summing amplifier 185 with gain that varies as a function of the instantaneous amplitude of the audio signals. The precision rectifiers 130 and 135 generate unipolar signals with amplitudes the same as the instantaneous absolute amplitudes of the left and right audio signals. These signals are scaled and used to control the gains of the voltage controlled amplifiers 140 and 145.

The variably amplified subliminal signals are then summed with the left and right audio signals by summing amplifiers 120 and 125 and the composite signals are AC coupled to the outputs 40 and 45 by capacitors 150 and 152 respectively. The inputs to the summing amplifiers 120 and 125 from the voltage controlled amplifiers 140 and 145 are scaled with respect to the left and right audio signal inputs so that the subliminal signals are continuously maintained at a consciously inaudible level of preferably about −30 dB with respect to the levels of the audio signals.

The security tone detect/decode unit 170 also receives the amplified message signal on line 162 and inputs the signal to the two tuned PLL's. If, and only if, the error signal outputs of both PLL's are low, indicating that both security tones are present, the gate control signal output by the detect/decode unit 170 on line 172 is high. A high gate control signal renders the gates 195 and 200 non-conductive. A low signal energizes the gates, which then shunt the control signals from the precision rectifiers 130 and 135 on lines 142 and 147 respectively to ground. This disables the voltage controlled amplifiers 140 and 145 from passing the subliminal signals output by the summing amplifier 185 on lines 186 and 187 and thus prevents the subliminal message signal from being mixed with the left and right audio signals. Accordingly, only the left and right audio signals are output on the left and right audio output lines 40 and 45.

Figure 4:
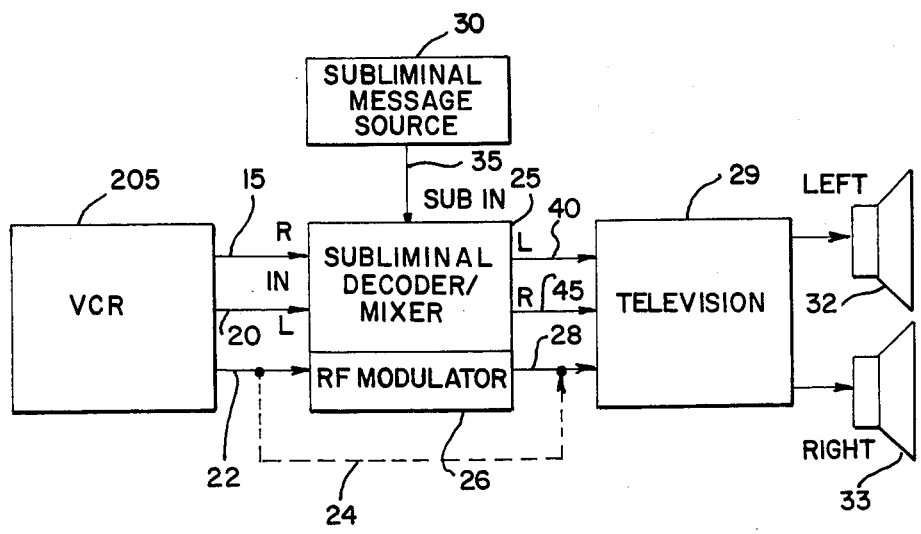
FIG. 4 is a block diagram illustrating an alternative embodiment of the subliminal decoder/mixer of FIGS. 1 and 2 which is adapted for use with a video cassette recorder and television.

FIG. 4 illustrates an alternative preferred embodiment of the subliminal decoder/mixer 25 which is adapted for use with an audio-video program source such as a video cassette recorder (VCR) 205 and an audio-video output device such as a television 29, for example. In this embodiment, the subliminal decoder/mixer 25 contains the same circuitry as illustrated in FIG. 2 and described above. The left and right audio signal inputs of the subliminal decoder/mixer 25 are connected to the left and right audio outputs 15 and 20 respectively of the VCR. The left and right audio outputs of the subliminal decoder/mixer 25 are input to the left and right audio inputs of television 29 if it is adapted to receive stereo and the signals are broadcast by left and right television speakers 32 and 33. If the television 29 is not stereo compatible, either the right or left audio output of the subliminal decoder/mixer 25 is connected to the monaural audio input of the television 29. If no such connection is provided, it is necessary to use a separate audio amplifier and speaker.

In addition, the subliminal decoder/mixer 25 also contains a conventional RF modulator 26 which receives the composite video output signal of the VCR 205 on a line 22. The RF modulator 26 converts the composite signal to a radio frequency signal suitable for display preferably on channel 3 or 4 of the television 29 in a manner well known to those skilled in the art, and outputs the signal to the television on line 28. Alternatively, if the VCR contains its own RF modulator or if the television 29 is adapted to receive the VCR composite video signal, the VCR video signal may be connected directly to the video input of the television 29 on a line 24, for example. Thus, in the alternative embodiment of FIG. 4, the listener may watch a favorite program, for example, while at the same time obtaining the benefits of auditory subliminal programming.

What have been described are certain aspects of auditory subliminal programming systems which constitute presently preferred embodiments of the invention. It is understood that the foregoing description and accompanying illustrations are merely exemplary and are in no way intended to limit the scope of the invention, which is defined solely by the appended claims and their equivalents. Various changes and modifications to the preferred embodiments will be apparent to those skilled in the art. Such changes and modifications may include, but are not limited to: the use of different security arrangements such as pseudo-random codes and corresponding detectors; the addition or deletion of signal components from the composite output signals; the use of various different types of audio program source and subliminal message source equipment such as tape decks, speech synthesizers, live input, phonographs, and the like; and the use of different output devices such as headphones or the like. Moreover, various analog components of the preferred embodiment can be replaced by equivalent digital components and vice versa. Such changes and modifications can be made without departing from the spirit and scope of the invention. Accordingly it is intended that all such changes and modifications be covered by the appended claims and equivalents.

We claim:

1. A subliminal decoder/mixer for use in an auditory subliminal programming system, comprising:
   means for receiving at least one audio program signal and at least one subliminal message signal;
   means responsive to the instantaneous amplitude of said audio program signal for rapidly varying the amplitude of said subliminal message signal; to maintain said signal at a selected consciously inaudible level relative to the level of said audio program signal; and
   means for combining said audio program signal and said subliminal message signal to produce at least one composite signal having an audio program component and a subliminal message component.

2. The subliminal decoder/mixer of claim 1 wherein said means for varying the amplitude of said subliminal message signal comprises:
   rectifier means for generating a control signal indicative of the instantaneous absolute amplitude of said audio program signal; and
   amplifier means responsive to said control signal for amplifying said subliminal message signal with gain that varies as a function of said control signal.

3. The subliminal decoder/mixer of claim 1 further comprising:
   signal generator means for generating at least one signal having a selected frequency; and
   means for combining said signal with said subliminal message signal to form a composite subliminal message signal.

4. The auditory subliminal programming system of claim 1 wherein said subliminal decoder/mixer means further comprises:

signal generator means for generating selected subsonic frequency signals; and means for combining said signals with said subliminal message signal to form a composite subliminal message signal.

5. A subliminal decoder/mixer for use in an auditory subliminal programming system, comprising:

means for receiving at least one audio program signal and at least one subliminal message signal;

means for combining said audio program signal and said subliminal message signal to produce at least one composite signal having an audio program component and a subliminal message component, the amplitude of the subliminal message component relative to the amplitude of the audio program component being such that only the audio program component is consciously audible;

means for detecting at least one predetermined security code in said subliminal message signal; and means responsive to said means for detecting for preventing said subliminal message signals from being combined with said audio program signal unless said at least one predetermined security code is detected.

6. The subliminal decoder/mixer of claim 5 wherein said at least one security code comprises at least one tone signal having selected frequency.

7. The subliminal decoder/mixer of claim 5 further comprising:

signal generator means for generating at least one signal having a selected frequency; and means for combining said signal with said subliminal message signal to form a composite subliminal message signal.

8. An auditory subliminal programming system, comprising:

audio program source means for generating at least one audio program signal;

subliminal message source means for generating at least one subliminal message signal;

subliminal decoder/mixer means for procesing said audio program signal and said subliminal message signal, said decoder/mixer means comprising:

means for receiving said audio program signal and said subliminal message signal;

means responsive to the instantaneous amplitude of said audio program signal for rapidly varying the amplitude of said subliminal message signal to maintain said signal at a selected consciously inaudible level relative to the level of said audio program signal; and means for combining said audio program and subliminal message signals to produce at least one composite signal having an audio program component and a subliminal message component;

audio amplifier means for receiving and amplifying said at least one composite signal; and audio speaker means for broadcasting said at least one composite signal.

9. The auditory subliminal programming system of claim 8 wherein said means for varying the amplitude of said subliminal message signal comprises:

rectifier means for generating a control signal indicative of the instantaneous absolute amplitude of said audio program signal; and amplifier means responsive to said control signal for amplifying said subliminal message signal with gain that varies as a function of said control signal.

10. An auditory subliminal programming system, comprising:

audio program source means for generating at least one audio program signal;

subliminal message source means for generating at least one subliminal message signal;

subliminal decoder/mixer means for processing said audio program signal and said subliminal message signal, said decoder/mixer means comprising:

means for receiving said audio program signal and said subliminal message signal;

means for combining said audio program and subliminal message signals to produce at least one composite signal having an audio program component and a subliminal message component, the amplitude of the subliminal message component relative to the amplitude of the audio program component being such that only the audio program component is consciously audible;

means for detecting at least one predetermined security code in said subliminal message signal; and means responsive to said means for detecting for preventing said subliminal message signal from being combined with said audio program signal unless said at least one predetermined security code is detected;

audio amplifier means for receiving and amplifying said at least one composite signal; and audio speaker means for broadcasting said at least one composite signal.

11. The auditory subliminal programming system of claim 10 wherein said subliminal decoder/mixer means further comprises:

signal generator means for generating at least one signal having selected frequency; and means for combining said signal with said subliminal message signal to form a composite subliminal message signal.

12. The auditory subliminal programming system of claim 10 wherein said at least one predetermined security code comprises at least one tone signal having selected frequency.

13. An auditory subliminal programming system, comprising:

subliminal message encoder means for combining a subliminal message with at least one predetermined security code to produce an encoded subliminal message; and subliminal decoder/mixer means for receiving a subliminal message and an audio program, said decoder/mixer comprising decoding means for detecting whether said subliminal message is encoded with said predetermined security code, and mixing means responsive to said decoding means for combining said subliminal message with said audio program to produce at least one composite signal having a consciously audible audio program component and a subconsciously audible subliminal message component only if said decoding means detects said security code.

14. The auditory subliminal programming system of claim 13 wherein said subliminal encoder means comprises at least one oscillator means for generating at least one said security code comprising a tone signal haveing selected frequency.

15. A subliminal message encoder system for use in an auditory subliminal programming system, comprising:

means for generating at least one subliminal message signal;

means for generating at least one security code;

combining means for combining said at least one security code and said subliminal message signal to produce an encoded subliminal message signal; and recording means for recording said encoded subliminal message signal.

16. An audio-video subliminal programming system, comprising:

audio-video program source means for generating audio and video program signals;

subliminal message source means for generating at least one auditory subliminal message signal;

subliminal decoder/mixer means for processing said audio and video program signals and said subliminal message signal, said decoder/mixer means comprising:

means for receiving said audio and video program signals and said subliminal message signal;

means responsive to the instantaneous amplitude of said audio program signal for rapidly varying the amplitude of said subliminal message signal to maintain said signal at a selected consciously inaudible level relative to the level of said audio program signal;

means for combining said audio program signal and said subliminal message signal to produce at least one composite signal having an audio program component and a subliminal message component; and modulator means for modulating said video program signal for reception by a television video display means;

audio amplifier means for receiving and amplifying said at least one composite signal;

audio speaker means for broadcasting said at least one composite signal; and television video display means for receiving and displaying the modulated video program signal.

17. The audio-video subliminal programming system of claim 16 wherein said means for varying the amplitude of said subliminal message signal comprises:

rectifier means for generating control signals indicative of the instantaneous absolute amplitude of said audio program signal; and amplifier means responsive to said control signal for amplifying said subliminal message signal with gain that varies as a function of said control signal.

18. The audio-video subliminal programming system of claim 16 wherein said subliminal decoder/mixer means further comprises:

signal generator means for generating at least one signal having selected frequency; and means for combining said signal with said subliminal message signal to form a composite subliminal message signal.

19. An audio-video subliminal programming system, comprising:

audio-video program source means for generating audio and video program signals;

subliminal message source means for generating at least one auditory subliminal message signal;

subliminal decoder/mixer means for processing said audio and video program signals and said subliminal message signal, said decoder/mixer means comprising:

means for receiving said audio and video program signals and said subliminal message signal;

means for combining said audio program signal and said subliminal message signal to produce at least one composite signal having an audio program component and a subliminal message component, the amplitude of the subliminal message component relative to the amplitude of the audio program component being such that only the audio program component is consciously audible;

means for detecting at least one predetermined security code in said subliminal message signal;

means responsive to said means for detecting for preventing said subliminal message signal from being combined with said audio program signal unless said at least one predetermined security code is detected; and modulator means for modulating said video program signal for reception and display by a television video display means;

audio amplifier means for receiving and amplifying said at least one composite signal;

audio speaker means for broadcasting said at least one composite signal; and television video display means for receiving and displaying the modulated video program signal.

20. The audio-video subliminal programming system of claim 19 wherein said at least one predetermined security code comprises at least one tone signal having selected frequency.

21. The audio-video subliminal programming system of claim 19 wherein said subliminal decoder/mixer means further comprises:

signal generator means for generating at least one signal having selected frequency; and means for combining said signal with said subliminal message signal to form a composite subliminal message signal.

* * * * *